United States Patent

Bru-Magntez et al.

[11] Patent Number: 5,480,652
[45] Date of Patent: Jan. 2, 1996

[54] EFFERVESCENT PHARMACEUTICAL COMPOSITION CONTAINING IBUPROFEN AND ITS METHOD OF PREPARATION

[75] Inventors: Nicole Bru-Magntez, Paris; Jean-Francois Cordoliani, Layrac; Gérard Thauvin, Agen; Jehan-Yves Drouin, Verrieres le Buisson, all of France

[73] Assignee: Laboratoires UPSA, Agen, France

[21] Appl. No.: 14,530

[22] Filed: Feb. 8, 1993

[30] Foreign Application Priority Data

Dec. 9, 1992 [FR] France .................................. 92 14851

[51] Int. Cl.⁶ .............................. A61K 9/46; A61K 9/14
[52] U.S. Cl. .......................... 424/466; 424/489; 424/501; 514/960
[58] Field of Search ..................................... 424/466, 489, 424/501; 514/960

[56] References Cited

U.S. PATENT DOCUMENTS 5,032,384  7/1991  Yeh et al. .................................. 424/49
5,178,878  1/1993  Vuelling et al. ......................... 424/466
5,180,590  1/1993  Carcano et al. ......................... 424/466

Primary Examiner—Jyothsna Venkat
Attorney, Agent, or Firm—Meserole, Pollack, Pollack & Scheiner

[57] ABSTRACT

The present invention relates to a novel pharmaceutical composition for the preparation of effervescent powders or tablets incorporating ibuprofen or one of its pharmaceutically acceptable salts as the active ingredient.

This composition comprises:

an effective amount of ibuprofen or one of its pharmaceutically acceptable salts;

a pharmaceutically acceptable effervescent system comprising at least one alkaline carbonate and at least one organic acid, preferably in a sufficient amount to give a pH below about 8; and at least one pharmaceutically acceptable antioxidant in a sufficient amount to stabilize the ibuprofen.
This composition has a remarkable stability both in powder form and in tablet form.

8 Claims, No Drawings

EFFERVESCENT PHARMACEUTICAL COMPOSITION CONTAINING IBUPROFEN AND ITS METHOD OF PREPARATION

The present invention relates to a novel effervescent pharmaceutical composition containing ibuprofen as the active ingredient, and to its method of preparation.

2-(4-Isobutylphenyl)propionic acid, known by the name ibuprofen, is a well-tolerated drug possessing analgesic, antipyretic and antiinflammatory activities (Merck Index, 11th edition, no. 4812).

Various solutions have therefore been proposed, in the state of the art, for the preparation of ibuprofen-based drugs in the form of effervescent powders or tablets.

Thus the document FR-2 590 893 proposes a composition for the preparation of effervescent tablets or granules, comprising the following in parts by weight:

9 to 17% of ibuprofen,
17 to 33% of arginine,
20 to 35% of sodium or potassium bicarbonate
and
25 to 40% of sodium bitartrate,
the total being 100%.

Said document of the prior art presents the use of sodium bitartrate and arginine as obligatory for obtaining a good dissolution of the ibuprofen.

The document EP-A-0 228 164 proposes a composition for the preparation of an effervescent powder or tablet, comprising ibuprofen or one of its pharmaceutically acceptable salts, an effervescent pair of compounds capable of producing carbon dioxide in the presence of water, a surfactant and an insoluble hydrophilic polymer.

According to said document of the prior art, the ibuprofen is preferably coated with the insoluble hydrophilic polymer (advantageously consisting of microcrystalline cellulose) and it is indicated that, in the absence of such a polymer, the ibuprofen deposits on the walls of the container in which the effervescent composition is prepared.

It is also mentioned that the incorporation of a saccharide, preferably sucrose, makes it possible to improve the stability of the ibuprofen and the keeping quality of these compositions.

The document EP-A-351 353 proposes another composition for the preparation of effervescent powders or tablets, comprising:

200 to 800 mg of ibuprofen,
221.3 to 885.2 mg of the sodium salt of ibuprofen,
2100 to 8402 g of sodium bicarbonate and
0.450 to 1800 g of citric acid.

According to said document of the prior art, the use of specific proportions of ibuprofen, sodium bicarbonate and citric acid and the use of a specific granulation process (granulation in a fluidized bed granulator) make it possible to obtain completely soluble effervescent tablets of ibuprofen which do not have a bitter taste and do not cause irritation of the throat when taken.

The object of the present invention is to provide a novel composition for the preparation of effervescent powders or tablets of ibuprofen with improved stability.

It has in fact been found that ibuprofen degrades in the presence of and in contact with alkaline carbonates.

This interaction is particularly troublesome in the production of effervescent tablets, which requires:

on the one hand the presence of large amounts of alkaline carbonates to ensure rapid disaggregation of the tablet; and on the other hand a compression step which increases the contact between the ibuprofen and the alkali metal carbonates.

Thus, according to a first feature, the present invention relates to a pharmaceutical composition for the preparation of effervescent powders or tablets containing an effective amount of ibuprofen or one of its pharmaceutically acceptable salts as the active ingredient, and a pharmaceutically acceptable effervescent system comprising at least one alkaline carbonate and at least one organic acid, said composition comprising at least one pharmaceutically acceptable antioxidant in a sufficient amount to stabilize the ibuprofen.

Thus the present invention is based on the surprising discovery of the fact that the stability of ibuprofen or its pharmaceutically acceptable salts in contact with alkaline carbonates can be considerably improved by prior treatment of the ibuprofen or its pharmaceutically acceptable salts with an antioxidant.

Within the framework of the present description and the claims, powders are understood as meaning any granulated or non-granulated mixture of components which is intended to be dissolved and/or suspended in water or else to be ingested directly or by any other appropriate means such as, for example, mixed with food.

It should be noted that the present invention applies preferentially to ibuprofen and to its insoluble salts such as, in particular, the calcium salt, but its principle can also be used for the preparation of powders or tablets incorporating soluble salts of ibuprofen.

Examples of alkaline carbonates which can be used within the framework of the present invention are sodium bicarbonate, potassium bicarbonate, carboxylysine, calcium carbonate, sodium carbonate, potassium carbonate and mixtures of these compounds.

Sodium bicarbonate will advantageously be used.

The organic acids which can be used within the framework of the present invention are compounds capable of reacting with alkaline carbonates to release carbon dioxide when they are brought into contact with a sufficient amount of water. Examples of suitable acids are citric acid, fumaric acid, adipic acid, tartaric acid and mixtures of these compounds.

The preferred acid is citric acid.

In one particular embodiment, the alkaline carbonate and organic acid will be used in sufficient amounts to give a pH below about 8 in the presence of water, preferably a pH of between 4 and 5.

In the preferred embodiment, where the effervescent system consists of a mixture of sodium bicarbonate and citric acid, the relative proportions by weight of these compounds in the effervescent system vary according to the desired pH after dissolution, as can be understood by those skilled in the art; for a pH of about 3 to about 7, for example, the ratio varies from about 20/80 to about 80/20.

According to one particular characteristic of the invention, this composition also comprises an effective amount of at least one internal dehydrating agent.

It has in fact been discovered that the presence of an internal dehydrating agent in the composition results in a further notable increase in the stability of ibuprofen and its pharmaceutically acceptable salts towards alkali metal carbonates, as will be explained below.

According to another particular characteristic, this composition also comprises a pharmaceutically acceptable diluent.

This diluent also plays a favorable role in the stabilization of ibuprofen and its pharmaceutically acceptable salts.

According to one particular characteristic of the invention, the above-mentioned antioxidant is selected from alpha-tocopherol, gamma-tocopherol, delta-tocopherol, extracts of natural origin which are rich in tocopherol, L-ascorbic acid and its sodium or calcium salts, palmityl-DL-ascorbic acid, propyl gallate, octyl gallate, dodecyl gallate, butylhydroxyanisole (BHA) gallate and butylhydroxytoluene (BHT) gallate.

In one currently preferred embodiment, the antioxidant will be alpha-tocopherol.

According to another particular characteristic of the invention, the internal dehydrating agent is magnesium citrate.

The purpose of the internal dehydrating agent is to trap any traces of water which may appear in the tablet. It has in fact been found that, when it comes into contact with alkali metal carbonates, ibuprofen degrades to generate water molecules, which further promote the degradation process.

According to another particular characteristic of the invention, the diluent is lactose.

However, any other pharmaceutically acceptable diluent could be used, in particular sucrose. Magnesium citrate can also be used for this purpose.

The respective amounts of antioxidant, internal dehydrating agent and diluent may easily be determined by those skilled in the art and of course depend on the desired final pharmaceutical form.

In general, a composition according to the present invention for the preparation of tablets can contain the following, expressed in parts by weight per parts of ibuprofen or one of its pharmaceutically acceptable salts:

from 120 to 900 and preferably from 245 to 330 parts by weight of at least one alkaline carbonate;

from 150 to 1100 and preferably from 390 to 475 parts by weight of at least one organic acid;

from $21.10^{-3}$ to $84.10^{-3}$ parts by weight of antioxidant, in the case of alpha-tocopherol; and, if appropriate:

from 400 to 1000 and preferably from 500 to 800 parts by weight of at least one pharmaceutically acceptable diluent; and from 10 to 150 and preferably from 20 to 100 parts by weight of an internal dehydrating agent, in the case of magnesium citrate.

A currently preferred composition for tablets comprises the following, expressed in parts by weight per 100 parts of ibuprofen:

270 parts by weight of at least one alkaline carbonate, preferably sodium bicarbonate;

450 parts by weight of at least one organic acid, preferably citric acid;

$42.10^{-3}$ parts by weight of alpha-tocopherol;

680 parts by weight of a diluent, preferably lactose; and 25 parts by weight of magnesium citrate.

In general, a composition according to the present invention for the preparation of powders can contain the following, expressed in parts by weight per 100 parts of ibuprofen or one of its pharmaceutically acceptable salts:

from 25 to 1200 and preferably from 270 to 585 parts by weight of at least one alkaline carbonate;

from 40 to 1125 and preferably from 315 to 675 parts by weight of at least one organic acid;

from $21.10^{-3}$ to $84.10^{-3}$ parts by weight of antioxidant, in the case of alpha-tocopherol; and, if appropriate:

from 90 to 6000 and preferably from 200 to 2100 parts by weight of at least one pharmaceutically acceptable diluent; and from 0 to 100 and preferably from 20 to 50 parts by weight of an internal dehydrating agent, in the case of magnesium citrate.

A currently preferred composition for sachets comprises the following, expressed in parts by weight per 100 parts of ibuprofen:

75 parts by weight of at least one alkaline carbonate, preferably sodium bicarbonate;

225 parts by weight of at least one organic acid, preferably citric acid;

$42.10^{-3}$ parts by weight of alpha-tocopherol;

175 parts by weight of a diluent, preferably lactose; and 25 parts by weight of magnesium citrate.

According to a second feature, the present invention relates to a pharmaceutical preparation in the form of an effervescent powder or tablet, which contains a composition such as defined above, if appropriate in association with at least one customary additive selected from sweeteners, flavorings, colors and lubricants.

The choice of these additives and their amount may easily be determined by those skilled in the art.

A sweetener can be a natural sugar such as sucrose or sorbitol, or a synthetic product such as saccharin or aspartame. Saccharin will advantageously be used.

In a first embodiment, this pharmaceutical preparation will be in the form of an effervescent tablet containing an amount of effervescent composition, such as defined above, corresponding to 200 mg, 400 mg or 600 mg of ibuprofen per tablet.

In another embodiment, this pharmaceutical preparation will be in the form of a powder containing an amount of effervescent composition, such as defined above, corresponding to 200 mg, 400 mg or 600 mg of ibuprofen per dosage unit.

According to a third feature, the present invention relates to a process for the manufacture of a pharmaceutical preparation in the form of effervescent powders or tablets, such as defined above, which comprises:

a) treating ibuprofen or one of its pharmaceutically acceptable salts with an effective amount of at least one pharmaceutically acceptable antioxidant, preferably by spraying it with a solution or emulsion containing the antioxidant;

b) premixing the constituents forming the effervescent system, preferably in the form of granules;

c) premixing the other constituents of the pharmaceutical form, preferably in the form of powders; and d) mixing the products resulting from the previous steps a), b) and c).

The pharmaceutical form obtained on completion of the above-mentioned process may be used directly in powder form and packaged for example in a sachet.

This pharmaceutical form may also be presented as a tablet after a traditional compression step.

In the above-mentioned step a) for treating the ibuprofen, a solution or emulsion containing the antioxidant will be used.

In the case of alpha-tocopherol, which is hydrophobic, it is advantageous to emulsify it in an appropriate solvent such as, for example, water or an organic solvent which is compatible with ibuprofen, i.e. in which ibuprofen is only slightly soluble.

Various emulsifiers conventionally used in pharmacy can also be used to produce this emulsion.

A mixture of sodium docusate and polyvinylpyrrolidone has proved particularly preferable.

The treatment of the ibuprofen with the antioxidant will preferably be carried out by spraying with the emulsion containing the antioxidant, using the different technologies conventionally used in the pharmaceutical industry, such as, for example, a planetary mixer, a vacuum mixer-granulator, a fluidized bed or else a shearing mixer, or a turbine.

Advantageously, the components of the effervescent system will be subjected to prior granulation, either together or separately, in an appropriate solvent (water, alcohol, methylene chloride, isopropanol or a mixture thereof).

The different ingredients of the pharmaceutical form, other than the ibuprofen treated with the antioxidant and the effervescent system, will preferably be mixed in powder form.

In one variant, at least one internal dehydrating agent, such as magnesium citrate, is added as one of the constituents of the pharmaceutical preparation.

The present invention will be illustrated by the following non-limiting Examples, in which the constituents are given in parts by weight relative to 100 parts by weight of ibuprofen:

EXAMPLE 1

Step a: Treatment of the ibuprofen with the antioxidant

Alpha-tocopherol ($42.10^{-3}$), sodium docusate ($75.10^{-3}$) and polyvinylpyrrolidone ($375.10^{-3}$) are mixed in water to give an emulsion.

The resulting emulsion is sprayed on to the ibuprofen (100) and the resulting product is dried under vacuum.

Step b: Granulation

The various components to be granulated [sodium bicarbonate (300) - citric acid (500)] are introduced into a mixer-granulator.

The granulation liquid is then sprayed on to the bed of powder.

After this granulation phase, the mixture obtained is dried in a fluidized bed.

The granules obtained are sized by means of a grid.

Step c: Final mixing

The constituents resulting from phases a and b are mixed with the other ingredients:

saccharin sodium: 7.5 flavoring: 15 lactose: 225 magnesium citrate: 50 colloidal silica: $5.10^{-1}$

The products resulting from the above-mentioned steps a to c are mixed for a period of about thirty minutes.

The product obtained is in the form of a dry powder which can be used directly for the preparation of tablets.

In a separate step, 3.4 gram portions of the product obtained were compressed in a tablet press to produce effervescent tablets.

EXAMPLE 2

Effervescent powders or tablets having the following composition were prepared by the procedure described above:

Examples of tablets

|  | Example 2 | Example 3 | Example 4 | Example 5 | Example 6 |
| --- | --- | --- | --- | --- | --- |
| a-Tocopherol | $42 \cdot 10^{-3}$ | $84 \cdot 10^{-3}$ | $21 \cdot 10^{-3}$ | $42 \cdot 10^{-3}$ | $42 \cdot 10^{-3}$ |
| Sodium docusate | $75 \cdot 10^{-3}$ | $100 \cdot 10^{-3}$ | $50 \cdot 10^{-3}$ | $80 \cdot 10^{-3}$ | $70 \cdot 10^{-3}$ |
| PVP | $375 \cdot 10^{-3}$ | $350 \cdot 10^{-3}$ | $400 \cdot 10^{-3}$ | $330 \cdot 10^{-3}$ | $420 \cdot 10^{-3}$ |
| Ibuprofen | 100 | 100 | 100 | 100 | 100 |
| Sodium bicarbonate | 585 | 675 | 225 | 270 | 245 |
| Citric acid | 315 | 305 | 675 | 450 | 285 |
| Saccharin sodium | 10 | 10 | 5 | 5 | 10 |
| Flavoring | 20 | 20 | 10 | 5 | 15 |
| Lactose | 820 | — | 520 | 720 | 780 |
| Dextrose | — | — | 100 | — | — |
| Mannitol | — | 600 | — | — | — |
| Magnesium citrate | 100 | 100 | 15 | 20 | 20 |
| Sodium benzoate | — | — | 10 | — |  |

Examples of powder for sachets

|  | Example 1 | Example 2 | Example 3 | Example 4 |
| --- | --- | --- | --- | --- |
| α-Tocopherol | $21 \cdot 10^{-3}$ | $70 \cdot 10^{-3}$ | $30 \cdot 10^{-3}$ | $30 \cdot 10^{-3}$ |
| Sodium docusate | $5 \cdot 10^{-2}$ | $10 \cdot 10^{-2}$ | $5 \cdot 10^{-2}$ | $7 \cdot 10^{-2}$ |
| PVP | 0.5 | 1 | 0.8 | 0.7 |
| Ibuprofen | 100 | 100 | 100 | 100 |
| Sodium bicarbonate | 75 | 160 | 375 | 125 |
| Citric acid | 225 | 40 | 1125 | 375 |
| Saccharin sodium | 10 | 0 | 5 | 5 |
| Flavoring | 0 | 50 | 50 | 50 |
| Lactose | 200 | 4000 | 2000 | 2500 |
| Magnesium citrate | 25 | 25 | 25 | 0 |
| Colloidal silica | — | — | $5 \cdot 10^{-1}$ | — |

What is claimed is:

1. A composition for the preparation of effervescent tablets, which comprises, per 100 parts by weight of ibuprofen or pharmaceutically acceptable salt:

from 150 to 1100 parts by weight of an organic acid selected from the group consisting of citric acid, fumaric acid, adipic acid, tartaric acid and mixtures thereof;

from 120 to 900 parts by weight of an alkaline carbonate capable of reacting with said organic acid to generate carbon dioxide gas selected from the group consisting of alkali metal carbonates, and calcium carbonate;

from 0.021 to 0.084 parts by weight of alpha-tocopherol as said antioxidant, and, optionally:

from 400 to 1000 parts by weight of a pharmaceutically acceptable diluent selected from the group consisting of lactose, sucrose and magnesium citrate; and from 10 to 150 parts by weight of magnesium citrate as internal dehydrating agent.

2. A composition according to claim 1, which comprises, per 100 parts by weight of ibuprofen or pharmaceutically acceptable salt:

from 390 to 475 parts by weight of said organic acid;

from 245 to 330 parts by weight of said alkaline carbonate;

from 0.021 to 0.084 parts by weight of alpha-tocopherol; and, optionally:

from 500 to 800 parts by weight of said pharmaceutically acceptable diluent; and from 20 to 100 parts by weight of magnesium citrate.

3. A composition according to claim 1 which comprises per 100 parts by weight of ibuprofen or pharmaceutically acceptable salt:

450 parts by weight of said organic acid;

270 parts by weight of said alkaline carbonate;

0.042 parts by weight of alpha-tocopherol;

80 parts by weight of said diluent; and 25 parts by weight of magnesium citrate.

4. A composition according to claim 3, wherein said organic acid is citric acid, said alkaline carbonate is sodium bicarbonate and said diluent is lactose.

5. A composition for the preparation of effervescent powders, which comprises, per 100 parts by weight of ibuprofen or pharmaceutically acceptable salt thereof:

from 40 to 1125 parts by weight of an organic acid selected from the group consisting of citric acid, fumaric acid, adipic acid, tartaric acid and mixtures thereof;

from 25 to 1200 parts by weight of an alkaline carbonate capable of reacting with said organic acid to generate carbon dioxide gas selected from the group consisting of alkali metal carbonates, and calcium carbonate;

from 0.021 to 0.084 parts by weight of alpha-tocopherol as said antioxidant, and, optionally:

from 90 to 6000 parts by weight of a pharmaceutically acceptable diluent selected from the group consisting of lactose, sucrose, magnesium citrate and mixtures thereof; and from 0 to 100 parts by weight of magnesium citrate as an internal dehydrating agent.

6. A composition according to claim 5, which comprises, per 100 parts by weight of ibuprofen or pharmaceutically acceptable salt:

from 315 to 675 parts by weight of said organic acid;

from 270 to 585 parts by weight of said alkaline carbonate;

from 0.021 to 0.084 parts by weight of alpha-tocopherol; and, optionally:

from 200 to 2100 parts by weight of said pharmaceutically acceptable diluent; and from 20 to 50 parts by weight of magnesium citrate as internal dehydrating agent.

7. A composition according to claim 5 which comprises:

225 parts by weight of said organic acid;

75 parts by weight of said alkaline carbonate;

0.042 parts by weight of alpha-tocopherol;

175 parts by weight of a diluent; and 25 parts by weight of magnesium citrate.

8. A composition according to claim 5, wherein said organic acid is citric acid, said alkaline carbonate is sodium bicarbonate and said diluent is lactose.

* * * * *

UNITED STATES PATENT AND TRADEMARK OFFICE
CERTIFICATE OF CORRECTION

PATENT NO. : 5,480,652

DATED : January 2, 1996

INVENTOR(S) : NICOLE BRU-MAGNIEZ et al

It is certified that error appears in the above-identified patent and that said Letters Patent is hereby corrected as shown below:

Title page:

Item: [75] Inventors: change "Nicole Bru-Magntez" to

--Nicole Bru-Magniez--.

Signed and Sealed this

Twenty-sixth Day of March, 1996

Attest:

BRUCE LEHMAN

*Attesting Officer*         *Commissioner of Patents and Trademarks*